United States Patent
Goswami

[11] Patent Number: 5,835,840
[45] Date of Patent: Nov. 10, 1998

[54] PHOTOCATALYTIC SYSTEM FOR INDOOR AIR QUALITY

[75] Inventor: D. Yogi Goswami, Gainesville, Fla.

[73] Assignee: Universal Air Technology, Lake Hopatcong, N.J.

[21] Appl. No.: 524,284

[22] Filed: Sep. 6, 1995

[51] Int. Cl.[6] ............................................. B01J 19/12
[52] U.S. Cl. ...................................... 422/186.3; 204/24
[58] Field of Search ................................. 422/186.3, 24

[56] References Cited

U.S. PATENT DOCUMENTS

| | | | |
|---|---|---|---|
| 2,265,252 | 12/1941 | Schaefer | 261/30 |
| 2,628,083 | 2/1953 | Rense | 261/14 |
| 2,638,644 | 5/1953 | Rauhut | 21/74 |
| 3,973,927 | 8/1976 | Furchner et al. | 422/22 X |
| 4,102,654 | 7/1978 | Pellin | 55/102 |
| 4,306,358 | 12/1981 | King, Jr. | 34/487 |
| 4,437,954 | 3/1984 | Sammells et al. | 422/186 X |
| 4,464,336 | 8/1984 | Hiramoto | 422/24 |
| 4,554,719 | 11/1985 | Lewis | 29/890.039 |
| 4,694,179 | 9/1987 | Lew et al. | 422/24 X |
| 4,734,111 | 3/1988 | Hoffmann et al. | 435/266 |
| 4,750,917 | 6/1988 | Fuji | 422/24 X |
| 4,804,768 | 2/1989 | Keutenedjian | 250/436 |
| 4,859,594 | 8/1989 | Portier | 435/172.1 |
| 4,892,712 | 1/1990 | Robertson et al. | 422/24 X |
| 4,931,654 | 6/1990 | Horng | 250/436 |
| 4,955,208 | 9/1990 | Kawashima et al. | 422/122 X |
| 4,966,759 | 10/1990 | Robertson et al. | 422/186 |
| 4,990,311 | 2/1991 | Hirai et al. | 422/4 |
| 5,032,241 | 7/1991 | Robertson et al. | 204/157.15 |
| 5,045,288 | 9/1991 | Raupp et al. | 422/186.3 |
| 5,069,885 | 12/1991 | Ritchie | 422/186 |
| 5,151,252 | 9/1992 | Mass | 422/24 X |
| 5,186,907 | 2/1993 | Yanagai et a. | 422/186.3 |
| 5,200,156 | 4/1993 | Wedekamp | 422/24 X |
| 5,219,534 | 6/1993 | Reynolds | 422/186.3 |
| 5,225,167 | 7/1993 | Wetzel | 422/121 |
| 5,227,053 | 7/1993 | Bryan | 210/143 |
| 5,260,036 | 11/1993 | Weigold et al. | 422/186.3 |
| 5,262,066 | 11/1993 | Van Soye et al. | 422/24 X |
| 5,397,552 | 3/1995 | Weigold et al. | 422/186.3 |
| 5,413,768 | 5/1995 | Stanley, Jr. | 422/24 X |
| 5,433,763 | 7/1995 | Shagott et al. | 55/323 |
| 5,449,443 | 9/1995 | Jacoby et al. | 204/157.3 |
| 5,456,740 | 10/1995 | Snow et al. | 96/11 |
| 5,501,801 | 3/1996 | Zhang et al. | 210/748 |
| 5,554,300 | 9/1996 | Butters et al. | 210/748 |
| 5,589,132 | 12/1996 | Zippel | 422/24 |
| 5,604,339 | 2/1997 | Tabatabale-Raissi et al. | 204/157.3 |

FOREIGN PATENT DOCUMENTS

| | | |
|---|---|---|
| B-76028/87 | 1/1988 | Australia . |
| 63-80833 | 4/1988 | Japan . |
| 1-234729 | 9/1989 | Japan . |
| 2207824 | 8/1990 | Japan . |
| 3106420 | 5/1991 | Japan . |
| 94/11092 | 5/1994 | WIPO . |

OTHER PUBLICATIONS

Matthews, *Solar Energy,* 38(6), 405–13 (1987).
Trivedi, *Photocatalytic Disinfection of Airbourne Microorganisms* (Univ. of Florida, Sep. 6, 1994).

(List continued on next page.)

Primary Examiner—Daniel J. Jenkins
Attorney, Agent, or Firm—Lerner, David, Littenberg, Krumholz & Mentlik

[57] ABSTRACT

A system to disinfect and detoxify indoor duct-transported air to improve the quality thereof. A reactor is provided across a duct or housing and consists of a coated surface along the airstream path on which a semiconductor catalyst such as $TiO_2$ has been coated. Ultraviolet lamps are installed in the reactor such that the catalyst is exposed to UV rays as the air passes over it. As the photons of ultraviolet light are absorbed on the $TiO_2$ catalyst in the presence of water molecules in the air, hydroxyl radicals are created, which, in turn, cause the destruction of chemical and microbiological contaminants in the air. A relative humidity of 50%, under specific conditions of residence time provides an efficient number of water molecules to cause inactivation of microorganisms. The catalyst may be fixed on the matrix or on the surface of the duct as long as the ultraviolet light is incident on the catalyst as the air moves across it.

20 Claims, 2 Drawing Sheets

OTHER PUBLICATIONS

Sabate et al., *J. Catal.,* 127, 167–77 (1991).

Suzuki, "Photocatalytic Air Purification on $TiO_2$ Coated Honeycomb Support," *Photocat. Purification and Treat. of Water and Air* (Ollis and Al–Ekabi, Elsevier Sci. Pubs. 1993) 421–434.

Fujishama et al., "Biochemical Application of $TiO^2$ Photocatalysts," *Photocat. Purification and Treat. of Water and Air* (Ollis and Al–Ekabi, Eds., Elsevier Sci. Pubs. 1993) 193–205.

Wang et al., "Control of VOC Emissions from Air–Stripping Towers: Development of Gas–Phase Photocatalytic Process," *Photocat. Purification and Treat. of Water and Air* (Ollis and Al–Ekabi, Eds., Elsevier Sci. Pubs. 1993) 733–739.

Anderson et al., "Photodegradation of trichloroethylene in the gas phase using $TiO_2$ porous ceramic membrane," *Photocat. Purification and Treat. of Water and Air* (Ollis and Al–Ekabi, Eds., Elsevier Sci. Pubs. 1993) 405–420.

Wang et al., "Gas Phase Photocatalytic Process for the Control of VOC Emissions from Air–Stripping Towers," *Proc.–Annu. Conf., Am. Water Works Assoc.,* 585–605 (1993).

Ireland et al., "Inactivation of *Eschericha coli* by Titanium Dioxide Photocatalytic Oxidation," *Applied and Environmental Microbiology,* vol. 9, No. 5, pp. 1668–1607.

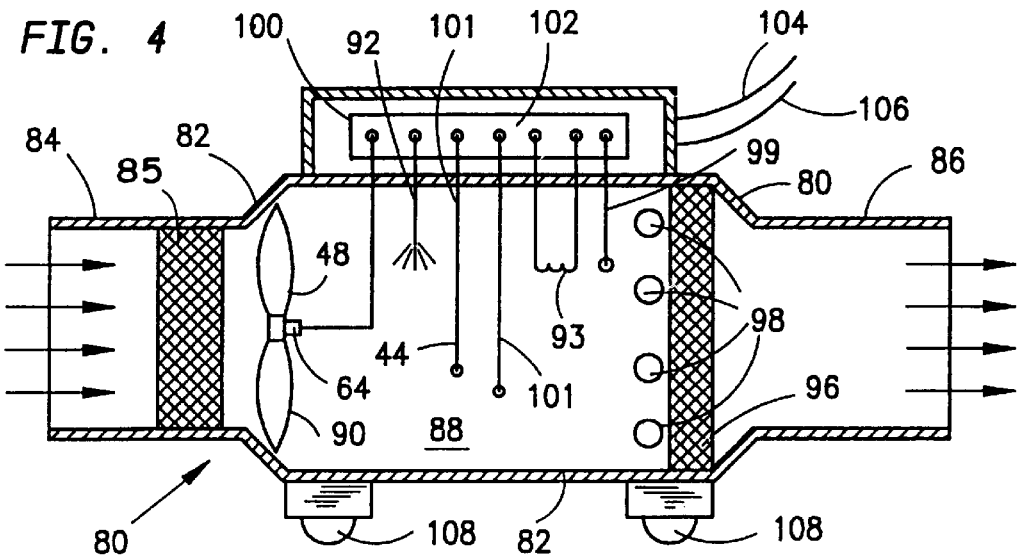
FIG. 4
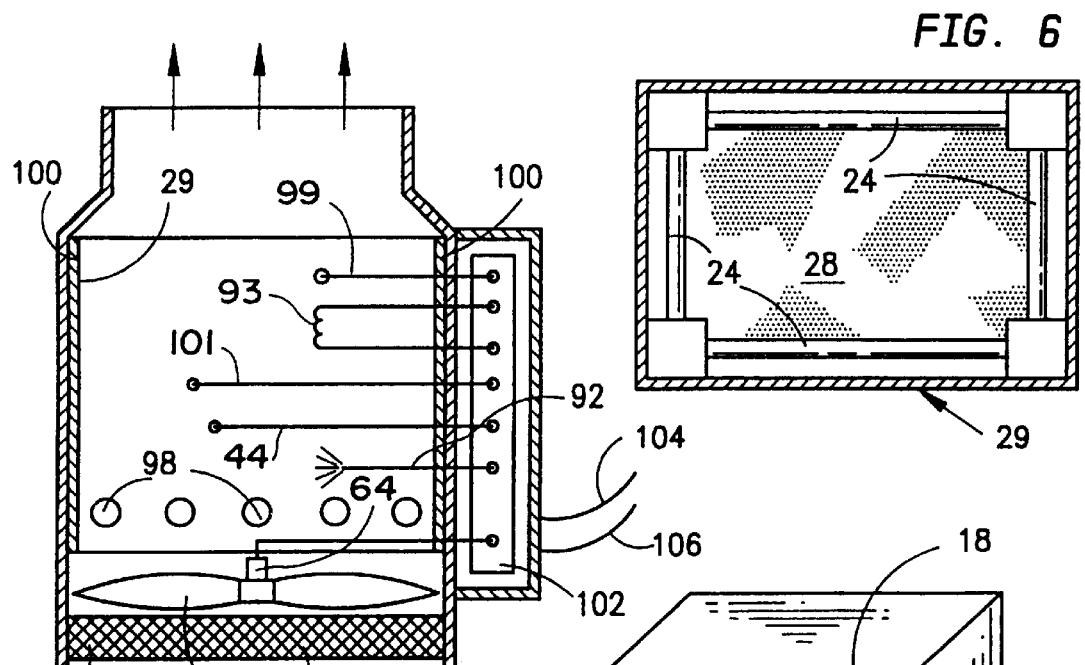
FIG. 5
FIG. 6
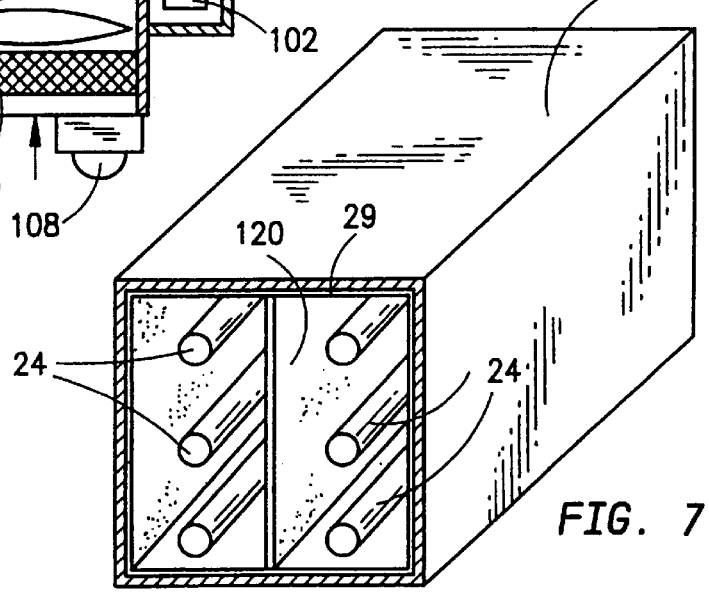
FIG. 7

PHOTOCATALYTIC SYSTEM FOR INDOOR AIR QUALITY

BACKGROUND OF THE INVENTION

Past studies have indicated that indoor air pollution, in some instances, poses a greater health risk than outdoor air pollution. In building circulating systems, pollutant levels from individual sources may not pose a significant risk by themselves. However, many buildings have more than one source that contributes to indoor air pollution. Illnesses resulting from such indoor pollutants are sometimes known as the "sick building syndrome." The causes of indoor air pollution are unwanted particulate matter, unwanted chemical substances and microbial contaminants. In the first two cases, conventional technology can oftentimes provide a solution by filtration and adequate ventilation. The problem of volatile organic compounds (VOCs) and microbiological contamination creates a more serious obstacle. In recent years, biological problems in indoor environments have received considerable attention. The Legionnaires' disease outbreak in Philadelphia in 1976 is probably the most publicized case of illness caused by indoor pollutants.

Biological contamination includes bacteria, molds, and viruses. A contaminated central air system can become a breeding ground for biological contaminants and the forced air can distribute the contaminants throughout the building.

Microbiological filters have been used for disinfection of air and other gases because of their low cost and ease of handling. These filters can be constructed to remove not only microorganisms but submicron particles as well. For efficient and economic operation of these filters, the aerosol content of the air to be filtered must be low. (Microorganisms, particles, or droplets of liquid dispersed in air can be referred to as aerosols.) A disadvantage of such filters is that they do not permanently remove the contaminants, but just transfer them to another medium; that is, the filter. Clogging will cause high pressure drops in the duct.

The prior art has recognized that high energy ultraviolet radiation (UV-C) exposure will destroy biological contaminants and toxic chemicals. Such UV-C treatment has worked well for disinfection but the indoor environment may also be contaminated with low level toxic chemicals such as formaldehyde, styrene, and toluene. Ultraviolet energy alone has proved ineffective in degrading these chemicals. Moreover, direct exposure to UV-C radiation is dangerous to humans causing concern for accidents if such radiation is used for indoor air. Interaction of UV-C with air can also produce ozone in the indoor air which is an unacceptable health risk.

FIELD OF THE INVENTION

This invention includes a photocatalytic oxidation process which involves the use of low energy photons of UV-A and a part of UV-B radiation (wavelength 300–400 nm) with titanium dioxide ($TiO_2$) as the photocatalyst. When properly designed and controlled with the techniques and equipment described herein, the combination will provide for the complete destruction of microorganisms in an airstream. This is an attractive solution because the process permanently removes the contaminants from the airstream. This invention provides such a solution.

The prior art is aware of utilizing UV lights on a filter coated with $TiO_2$ for its ability to destroy VOCs such as trichloroethylene (TCE) and non-volatile organic compounds such as polychlorinated biphenyls (PCBs) without creating any further hostile agents. For instance, U.S. Pat. No. 5,045,288 to Raupp and Dibble, and U.S. Pat. Nos. 4,892,712; 4,966,759; and 5,032,241 to Robertson and Henderson use UV to treat fluids and gases that contain pollutants. Neither of these patents render the control of relative humidity and residence time that is crucial to effective destruction of pollutants. The Robertson et al references teach a rolled-up filter having several thicknesses with the UV light penetrating the entire coil. The system taught by Raupp will work to destroy VOCs but will not work in the environment of this invention. This is because, in purification and detoxification of indoor air, bacteria and microbes are only effectively destroyed by the photocatalytic action of UV under controlled humidity and residence time conditions. Since microorganisms are living organisms, as opposed to VoCs which are not, the former can tolerate certain harsh conditions because of the built-in body defenses and succumb to only critically harsh conditions. The controls of this invention create the critically harsh conditions required to destroy the living microorganisms that are the major cause of Sick Building Syndrome.

The system of this invention is adapted for use within a normal air circulatory duct arrangement or as stand alone units when used within a building ventilation system, the air in the duct leading from a heating or cooling unit (hereinafter collectively referred to as an air conditioner) is forced by a blower through the duct system until it reaches the room registers. At other locations, are return ducts carrying the return air back to the air conditioning unit. It is within this system that bacteria and other microorganisms oftentimes develop. Due to the fact that the same air, for the most part, is constantly being recirculated, the contamination can be compounded with each round of circulation.

The air circulation in many buildings is continuous and is sometimes controlled by a thermostat of one type or another. In many buildings, circulation of the air continues whether or not the heating or cooling unit is actively performing. It is essential in a system of this type that the circulation flow is not seriously obstructed, but at the same time, proper conditions must be provided in which the photocatalytic destruction will work efficiently.

In order to achieve maximum efficiency, the air humidity and the residence time of the air within the UV illuminated (catalyst coated filter or catalyst lined duct) is controlled. The humidity factor is controlled by a humidifier/dehumidifier arrangement and the dwell factor, or residence time over the catalyst, is regulated by controlling the velocity or the flow rate of the air.

Maximum destruction will depend on several variables. For instance, the UV-$TiO_2$ phenomena will not provide adequate microbial destruction at humidity levels lower than about 40%. On the other hand, there is incomplete deactivation of organisms if the air being treated has a humidity in excess of 70%. A 50% humidity reading has been found to be effective. Also, without a proper residence time of the contaminated air in the catalytic filter, complete disinfection is not obtained. Herein described are reactor units that provide for a circulation system having means for enhancing the airstream characteristics with respect to speed and humidity for a particular UV light intensity so as to provide the most effective purification.

SUMMARY OF THE INVENTION

A primary objective of this invention is to provide a viable solution for indoor air purification and detoxification that can be used with new or already installed air duct systems.

Another objective of this invention is to provide a relatively inexpensive detoxification reactor which can be placed within the duct system of a troubled building. The reactor units can be disposed within one or several trunk ducts of the air distribution system or a reactor can be disposed in each duct leading to a room register.

A further objective of the invention is to provide a detoxification reactor unit which can be readily disposed in new circulation systems or as a modification to troubled circulation systems, or as a stand alone air filtration unit, or as an exit ventilation system or it can be used as an exit chamber for a vacuum cleaning system.

A still further objective of the invention is to provide a means by which the airflow rate through the reactor and the humidity of that airflow can be regulated so as to produce the maximum destruction efficiency of a UV light acting on a catalyst such as $TiO_2$.

Another important objective of the invention is to provide a photocatalytic oxidation system that not only destroys microorganisms but also decontaminates the organic chemicals, as well as odors resulting from microorganisms and volatile organic contaminants which are oftentimes found in indoor air.

A further objective of this invention is to provide stand-alone embodiments for purifying contaminated air departing from enclosures in which certain deleterious processes take place; for example, painting enclosures.

The stand-alone embodiment, in particular, also can be utilized in hospitals, doctor waiting rooms, rest rooms and in other locations where recirculation is feasible and odor-reduction and a high degree of purification are necessary to provide comfort to those using these facilities.

The above and other objects, features and advantages of the present invention will become clear from the following description of the preferred embodiments considered in conjunction with the accompanying drawings.

BRIEF DESCRIPTION OF THE DRAWINGS

FIG. 4 is a longitudinal cross-sectional view of a stand-alone embodiment;

FIG. 5 is a vertical variation of the stand-alone unit of FIG. 4;

FIG. 6 is a cross-section along the line 9—9 showing the UV lamps disposed about the perimeter of a duct; and FIG. 7 is a diagrammatic perspective view illustrating the positioning of the UV lamps with respect to catalyst carrier inserts.

DESCRIPTION OF THE PREFERRED EMBODIMENT

Figures 1, 2, 3:
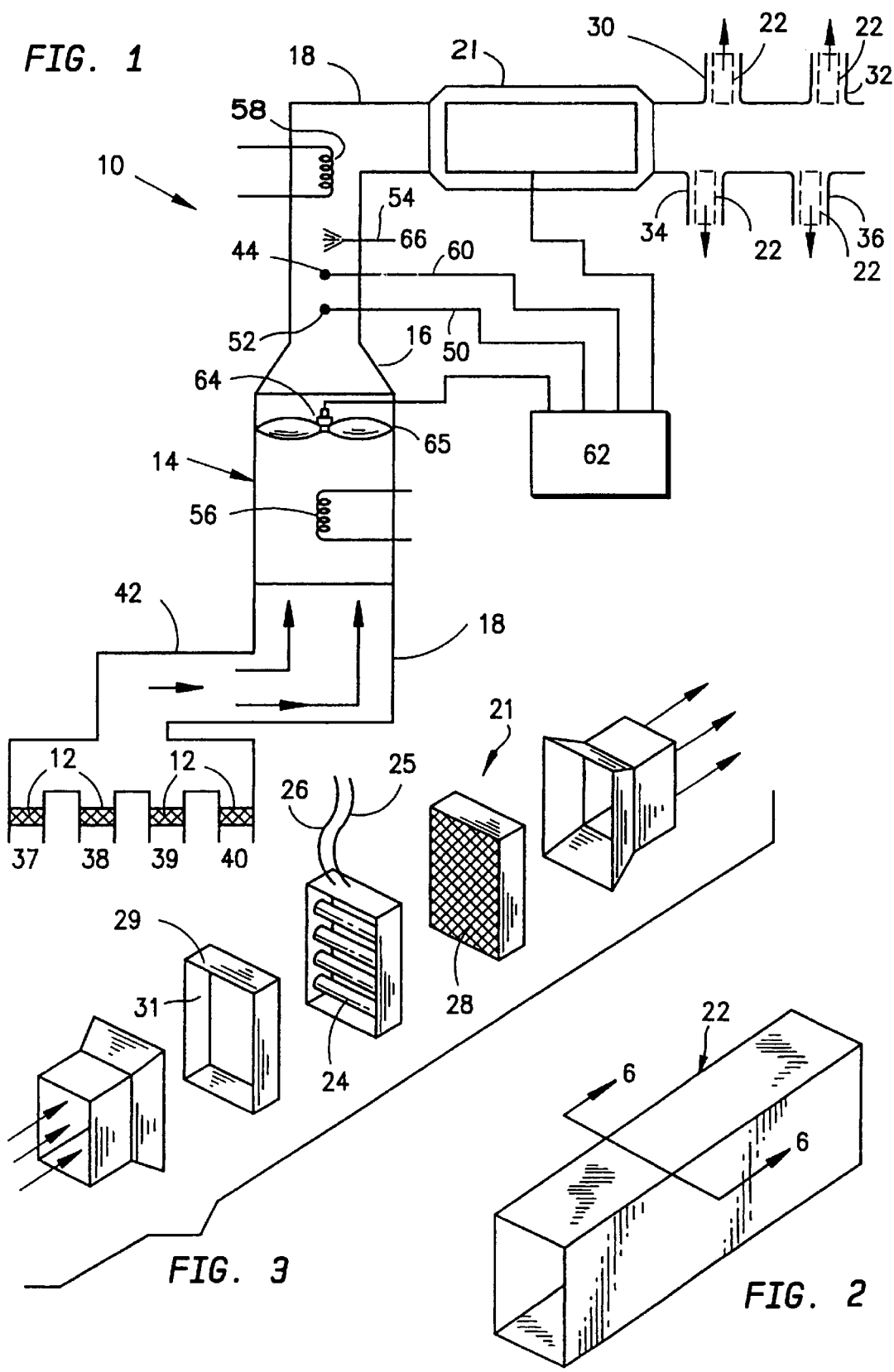
FIG. 1 is a diagrammatic-schematic of a typical heating/cooling duct system for a building with a reactor system of this invention incorporated therein.
FIG. 2 is a diagrammatic perspective view of a reactor unit for purposes of illustrating the cross-sections of other views.
FIG. 3 is an exploded diagrammatic view illustrating several of principal components of the reactor unit.

Referring now to the drawings wherein like elements are indicated by like numerals, the numeral 10 depicts the system of this invention. In most buildings, a blower/fan causes the air from the various zones of an air conditioned space to be drawn into a duct system via inlet openings and particle/aerosol filters 12. The air then can pass over the heating coil of the furnace (not shown) or the heating/cooling coil 56 of an air conditioner/heat pump of the air conditioning unit 14. The cooling coil will act as a dehumidifier since it condenses moisture from air as it cools the air.

The fan 65 of the air handling unit 14 will force the air passing over the coils 58 and 56, into a duct system 18. In FIG. 1 there is a master reactor 21 along the duct 18. In many installations this will be sufficient. However, in the embodiment of FIG. 1, there is also shown a series of reactor units 22 disposed in branch lines of duct system 18.

FIG. 2 diagrammatically illustrates the major components within reactor 21. These components will also be found in reactors 22. These major components are a coated liner 29, a bank of UV lamps 24 and a coated mesh or matrix of surfaces 28. In some instances only a coated liner or a coated mesh is used. Here both are used.

Various interiors of unit 22 can be seen in the Figures. A bank of UV lamps 24, connected to an electrical source by way of electrical leads 25 and 26 are available to each reactor unit 22. The leads 25 and 26 are shown in FIG. 3 but similar leads will be present in all embodiments. The UV rays from lamps 24, in these embodiments, strike a mesh 28 or a coated liner 29 which is coated with a catalyst such as $TiO_2$. Alternatively, or in addition to the filter, the UV rays are directed to a coated mesh 28 and coated duct sections 29 on either side thereof.

The mesh 28 may be made out of any material to which a catalyst, such as $Tio_2$ will adhere. The duct liners 29 may be made of any material that will allow the deposition and adherence of a catalyst such as $TiO_2$ on its interior surface 31. Some examples of such fibers and materials for the mesh include natural fibers such as cotton and wool, man-made and synthetic fibers such as rayon, polyester, polypropylene and teflon, and other materials such as flame resistant fibrous materials and carbons and all other functional fibrous materials. The mesh 28 is constructed in a loose woven, nonwoven, knitted or a combination thereof, configurations such that it allows relative free flow of air without an excessive pressure drop.

After passing through the reactors 22 and departing the branch conduits 30, 32, 34 and 36, the air is directed to room registers. Obviously, in a large building there may be several dozen conduits of the 30–36 type branching from a plurality of main ducts. Each room normally has an air return opening. The air is returned from each room via a series of ducts depicted by the numerals 37, 38, 39 and 40. These ducts contain the filters 12 and merge into a collector duct 42 which returns the air to the intake side of the air conditioning unit 14 where it may be recooled or reheated and returned to the duct system 18.

The retention time of the circulating air in the reactor 21 over the catalytic surfaces 28 or the coated duct section 29 is important. The speed of the air within the duct system is measured by way of a detector 44.

In FIG. 1 a conventional flow or speed detector 44 (a Mamac Anubar flow detector) is located in the main duct system 18. Speed detectors are oftentimes placed within each reactor 22 and it is that type of reactor which is described with respect to the stand alone units described hereinafter.

The faster the air speed, the less time air will be retained over the catalytic surfaces of mesh 28 or in contact with the coated surfaces 31 of lines 29. As speed or volumetric displacement is lowered, retention time increases. As stated previously, it is usually desirable to maintain air movement throughout the building at all times. Here, air speed is adjusted for a maximum destruction of the deleterious matter by controlling the filter retention time over the catalytic surface.

This retention time will vary depending on the air flow rate, the size of the ducts, the area of the catalytic surface and other physical characteristics. In any event, the air speed or volume flow rate is entered into a microprocessor 62 from the detector 44. The microprocessor 62 in turn will control the speed of fan motor 64 and thus the air displacement of fan 65. The blower speed is always adjusted to provide the required residence time. For example, an air speed of approximately 70 ft/min over 2 inches thick catalytic mesh provided good disinfection and destruction rates in the experiments conducted. The needed area of the mesh or the liner will depend on the expected concentrations of the contaminants and can be determined empirically for the installation involved.

Also disposed along the length of duct 18 is a humidifier/dehumidifier unit 50 (sold by Sun Chemical as Model SUN 13) controlled by a detector probe of the type sold by Mamac as Model HV-2222. If detector 52 detects that the moisture content in the air is less than 50%, a water spray or atomizer unit 54 is caused to spray enough moisture into the airstream as a fine mist to raise the humidity to approximately 50%. If the moisture content is over 70%, moisture is removed by a dehumidifier system here represented by cooling coil 56. Coil 56 can be a separate unit but in many instances, the coils of unit 14 can be utilized. A separate back-up coil 58 can also be provided.

As can be seen, an air purifying and detoxification system is described which has as its essential killing agent the reactor units 21 and 22. Unless the humidity and air displacement factors have been regulated the reactors will not function efficiently.

FIG. 1 discloses a master reactor 21 and branch reactors 22. In relatively small installations, only reactor 21 will be used. In relatively large installations only reactors 22 will be used. They are combined in FIG. 1 to show that the combination can also be employed.

The UV lamps are supported in any conventional fashion so that rays are directed on their respective catalytic surfaces. FIG. 3 shows a rectangular liner 29 disposed within a duct section. Its inner surface is coated with $TiO_2$, as indicated by the numeral 31.

Alternatively, a pair of coated liners may be disposed within a duct section on opposite sides of a filter/mesh with the UV lights also disposed interiorally of the duct on opposite sides of the filter/mesh, cross-wise of the duct. In yet another alternative, a single coated linet in combination with a single bank of UV lamps are disposed within the duct on one side of a filter/mesh, with the UV lamps disposed cross-wise of the duct and adjacent to the filter/mesh.

The essentials of this invention can be utilized independently of a duct system. Such a stand alone unit 80 is shown in FIG. 4. The unit 80 includes a housing 82 having an inlet 84 and an outlet 86. Intermediate the inlet and outlet is a chamber 88 that includes a control fan 90, a humidifier 92, a dehumidifier 93, a fan motor 64 for driving fan 48, a $TiO_2$ coated filter 96 upon which UV light is cast from a series of UV lamps 98. An air speed detector 99 determines the air flow displacement. A second chamber 100 is provided on the housing 82 to enclose a microprocessor 102. The electric power for the unit 80 is provided to the system through the control processor 102 via leads 104 and 106. The unit 80 may be operated without its own humidity control system if the proper humidity can be ensured by an air conditioning system external to the unit 80. The unit 80 may also be operated without the airspeed detector 99, if the unit 80 is designed and constructed with a constant air flow rate fan 48 matched with the cross sectional area of the housing 82 to provide the required residence time for the air flow over the catalyst.

The unit 80 can be supported by wheels 108 so that it can be easily moved to a position within the room where it is most likely to encourage air flow circulation throughout the entire room. Also, the unit can be utilized as an exhaust unit from a room in which undesirable fumes are present which one does not wish to exhaust into the atmosphere without treating them first. For instance, in paint shops or in other industrial plants, the unit 80 can be built into a roof or any exterior wall or it can be adapted for window support in the same fashion as a room air conditioner. In any event, contaminated air is cleansed before reaching the atmosphere.

Control and operation for the stand alone unit is the same as that previously described. When power is supplied, the fan 48 will draw air into the inlet 84. A particulate/aerosol filter 85 is provided to maintain the interior of the unit free of dirt that might damage coated mesh 96 or a coated liner if one is used in combination with a mesh. The UV lights 98 are illuminated at the same time the fan begins to rotate.

A detector 44 will measure air speed and that information is fed to microprocessor 102. The microprocessor will then adjust the rpm of the fan to ensure the proper residence time the air is subjected to the UV light while traversing the $TiO_2$ coated surfaces whether a liner or a mesh.

While this is occurring, the humidity of the incoming air is monitored by unit 101 and that data is sent to the microprocessor. If the air has a humidity of below 40%, the wetting unit or humidifier 92 is actuated until a 50% humidity reading is obtained. If the air has a humidity of above 70%, the dehumidifier 93, here utilizing a heating coil 93, is actuated until the humidity is lowered to 50%.

FIG. 5 is a vertical embodiment of a stand-alone unit. Here a particulate/aerosol filter 118 pre-screens the air. A series of UV lamps 98 are disposed opposite a catalyst coated liner or surface 100.

Again, the fan speed is controlled by the microprocessor via motor 64 which receives the input from detector 44. Humidity is adjusted in the same manner as described in FIG. 4.

When coated liners are used in any of the disclosed embodiments, it may be desirable to increase the coated surface area that are exposed to the UV. FIG. 10 shows how a coated insert 120 (or inserts) can be utilized to increase the surface area exposed to the UV rays. Note the UV lamps 24 in each chamber. The catalytic surface area can also be increased by suspending rigid or flexible catalytic inserts or strips from the housing or duct. They can be used to replace or supplement inserts such as 120.

FIG. 6 is a cross-section showing a perimeter disposed UV lamps adjacent to the filter 28.

In describing the system, reference has been made to several preferred embodiments and illustrative advantages of the present invention. Those skilled in the art, however, will recognize additions, deletions, modifications, substitutions and/or other changes without departing from the instant invention and appended claims.

I claim:

1. A system for destroying bacteria and VOC's in a building ventilation system that has ventilation ducts leading to and from an air conditioning unit, comprising:

a main duct leading from said unit and carrying an airstream therethrough;

a coated surface in said duct and having a particular length in the direction of air flow;

a titanium dioxide coating on said surface;

an ultraviolet light source for directing ultraviolet light on said surface as said airstream passes therethrough;

a humidity detector in said duct;

first means responsive to said detector for controlling the moisture of said airstream prior to its entering the area of said coated surface; and, second means for controlling the flow speed of said airstream to control the amount of time each volumetric unit of air dwells in the vicinity of said catalytic surface while being subjected to said ultraviolet light.

2. The system of claim 1 wherein said first means is a humidifier/dehumidifier unit.

3. The system of claim 1 wherein a blower at said unit pushes the air stream through said duct:

a motor for rotating said blower;

a third means for measuring the velocity of said air in said duct;

a motor control responsive to said third means for controlling the speed of said fan so as to control the amount of time each volummetric unit of air spends in the area of said coated surface while exposed to said ultraviolet light.

4. The system of claim 1 wherein the wave length of light source is between 300 and 400 nanometers.

5. The system of claim 1 where the catalyst is any semiconductor material, such as $ZnO_2$, or a catalyst further activated by a noble metal such as platinum.

6. The system of claim 1 wherein the wavelength of the light source includes the wavelength corresponding to the gaps of the catalyst used.

7. The system of claim 1 wherein said coated surface is an open mesh cross-wise of said main duct.

8. The system of claim 7 wherein said light source is a series of elongated UV lamps parallel to said mesh.

9. The system of claim 3 wherein said light source is a plurality of elongated tubes positioned lengthwise of said duct and spaced near said coated surface.

10. The system of claim 1 wherein said coated surface is a tubular liner inserted into said duct.

11. The system of claim 1 where the catalyst is any semiconductor material that is activated by a noble metal.

12. The system of claim 1 where the wavelength of the light source is of a wavelength harmless to human beings.

13. A process for detoxifying organic pollutants and destroying microorganisms in a gas including the steps of:

establishing a 50% humidity factor in said gas;

bringing said gas into contact with a photoreactive material within a duct or housing;

bathing said material with a light of a wavelength to activate said material; and controlling the residence time of said gas while it is in contact with said material while said material is bathed by said light.

14. The process of claim 13 wherein said light is an ultra-violet light.

15. The process of claim 13 wherein said photoreactive material is $TiO_2$.

16. The process of claim 15 wherein said photoreactive material is $TiO_2$.

17. A process for detoxifying organic pollutants and destroying microorganisms in a gas including the steps of:

providing a conduit through which said gas is moved;

providing a surface in said conduit that is coated with a photoreactive material;

subjecting said material with UV light while said gas in contact with said material; in contact with said material;

blowing said air through said conduit by mechanical means;

controlling said blowing so that the resident time said gas is in contact with material is adjustable;

adjusting said resident time to obtain maximum destruction of said microorganisms and organic pollutants; and setting the humidity of said gas to from between 50% to 60% prior to its coming into contact with said material.

18. The process of claim 17 wherein said gas is passed over a heating coil if humidity is too high.

19. The process of claim 17 wherein spraying a water mist into said gas is accomplished if said humidity is too low.

20. The process of claim 17 wherein a fan blows said gas and the process further includes the steps of: controlling the rotational speed of said fan.

* * * * *

UNITED STATES PATENT AND TRADEMARK OFFICE
CERTIFICATE OF CORRECTION

PATENT NO. : 5,835,840
DATED : November 10, 1998
INVENTOR(S) : Goswami

It is certified that error appears in the above-identified patent and that said Letters Patent is hereby corrected as shown below:

Column 2, line 16, "VoCs" should read --VOCs--

Column 4, line 30, Tio$_2$" should read --TiO$_2$--.

Column 6, line 19, "stand alone" should read --stand-alone--.

Column 6, line 49, "are" should read --is--.

Column 6, line 65, "VOC's" should read --VOCs--.

Column 7, line 32, "where" should read --wherein--.

Column 8, line 1, "where" should read --wherein--.

Column 8, line 3, "where" should read --wherein--.

Column 8, line 26, "gas in" should read --gas is in--.

Signed and Sealed this

Twenty-third Day of March, 1999

Attest:

Q. TODD DICKINSON

*Attesting Officer*   *Acting Commissioner of Patents and Trademarks*